(12) United States Patent
Khatib

(10) Patent No.: US 7,897,749 B2
(45) Date of Patent: Mar. 1, 2011

(54) DAIRY CATTLE BREEDING FOR IMPROVED MILK PRODUCTION TRAITS IN CATTLE

(75) Inventor: Hasan Khatib, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 102 days.

(21) Appl. No.: 11/179,581

(22) Filed: Jul. 13, 2005

(65) Prior Publication Data

US 2007/0015164 A1  Jan. 18, 2007

(51) Int. Cl.
C07H 21/04 (2006.01)
(52) U.S. Cl. ............ 536/24.33; 536/24.3; 536/23.1
(58) Field of Classification Search ............ None
See application file for complete search history.

(56) References Cited

U.S. PATENT DOCUMENTS

| | | | | |
|---|---|---|---|---|
| 5,925,525 | A * | 7/1999 | Fodor et al. | 506/3 |
| 5,962,260 | A | 10/1999 | Sawamura et al. | |
| 6,197,937 | B1 * | 3/2001 | Sawamura et al. | 530/388.22 |
| 2004/0081958 | A1 * | 4/2004 | Eilertsen et al. | 435/6 |
| 2004/0146890 | A1 * | 7/2004 | Matsuzaki et al. | 435/6 |

FOREIGN PATENT DOCUMENTS

| | | | | |
|---|---|---|---|---|
| WO | WO95/111995 | * | 5/1995 | 435/6 |
| WO | WO/02/053773 | * | 7/2002 | 435/6 |

OTHER PUBLICATIONS

GenBank Accession No. AC115105.2 GI:20219825 (Apr. 20, 2002.*
Mathialagan N et al, *Pepsin-inhibitory activity of the uterine serpins*, Proceedings of the National Academy of Sciences of the United States of America (1996) vol. 93 (24), pp. 13653-13658, NCBI Accession No. L22095.
Sawamura T et al, *An endothelial receptor for oxidized low-density lipoprotein*, Nature (1997) vol. 386(6620) pp. 73-77, NCBI Accession No. D89049.
Band MR et al, *An ordered comparative map of the cattle and human genomes*, Genome research (2000) vol. 10(9) pp. 1359-1368.

* cited by examiner

*Primary Examiner* — Steven C Pohnert
(74) *Attorney, Agent, or Firm* — Kening Li; Pinsent Masons LLP

(57) ABSTRACT

Nucleic acid molecules comprising a SNP site selected from the group consisting of position 1296 of bovine uterine milk protein (UTMP) coding sequence (SEQ ID NO: 1), position 213 of bovine signal transducer and activator of transcription (STAT1) coding sequence (SEQ ID NO: 2), position 8514 of the osteopontin (OPN) gene (SEQ ID NO: 3), or position 1070 of a bovine lectin-like oxidized LDL receptor (OLR1) coding sequence (SEQ ID NO: 4), which SNP indicates a desirable milk production trait in a dairy cattle. Also disclosed are an array or a kit comprising the same, a method for detecting the SNPs, a method for progeny testing of cattle, and a method for selectively breeding of cattle.

9 Claims, 5 Drawing Sheets

Figure 1
Coding sequence for Bovine Uterine milk protein (UTMP)

```
   1    ggctggattg ccgcagaaat gtcccacggg agaatgaatc tggccctgtc tctggtcttc
  61    atcctctgtg gcctgtttaa tagcatcttc tgtgaaaagc aacaacactc tcaaaagcac
 121    atgaacctag tcttattaaa gaaaatttca gctctctccc agaagatgga agctcaccct
 181    aaggattttg cccaagaatt gttcaaggct ttgataattg aggatcccag aaagaatatc
 241    atcttctccc ccatggccat gaccaccacc ctggccaccc tctccctggg gatcaagtct
 301    acaatgagaa cccaccaccc tgaggacctg aaacttgagc ccaaactgtt ggatgtgcac
 361    aagtacttac agcctctggt ccacgtgggg cgtgagctag tgaagcagaa ggtactgaag
 421    caccagcaca ttctctttat caacagaaaa atgatggtca accagatgct tctacagcag
 481    ataagcaagc tgcagggaat ggacatccag atgattgact ttacagatat agaaaaagcc
 541    aagaagacca tcagccacca tgtggctgaa aaaacacata cgaaaatcac aaacttaatc
 601    accgacctga accctgagac catcctgtgt cttgttaacc acattttctt caaaggcatc
 661    ttgaaaagag cttttcagcc caaactcacc cagaaggagg tcttctttgt gaatgaccaa
 721    accaaagtgc aggtggacat gatgagaaag acagaacgga tgctttacag ccggtcagag
 781    gagctacatg ctacgatggt taagatgcct tgcaaaggaa atgtgtccct aactctcatg
 841    cttccagatg ccggacaatt tgacactgat cttaaaaaga tgactgctaa gcgagctaaa
 901    cttcagaaaa tcagtgactt cagactggtg cgcttaattt tgcccaagtt gaagatctcc
 961    ttcaagataa actttaagca tctgcttccc aagattgacc caaacatat actgactgcc
1021    acagcaatct cacaggccat cacatcgaag gctcccctgc ctaatttgga ggccctacat
1081    caagctgaga tagagctgag cgagcacgcc ttaaccgtgg acacagccat tcacacagat
1141    aatctgttga aagtcccagt gaaggcaaag gaggtcccgg cggtcgtgaa agtcccaatg
1201    aaggcaaagg aggtcccggc ggtcgtgaaa gtcccaatga acacaaagga ggtcccagtg
1261    gtcgtgaaag tcccaatgaa cacaaggag gtcccagtgg tcgtgaaggt caacagaccc
1321    ttcttgctgt ttgtggagga tgagaagact caaagagacc tctttgtggg caaagtcctc
1381    aaccccaag ttgagtagag ccagggccac actgtgcagc acaggaactt agcaggccat
1441    gaataaaaag agtacaattc acc
```

Notes: The SNP at position 1179 is A/G. G is the reported by the original submitter. The SNP at position 1296 is A/G. A is the nucleotide reported by the original submitter. The two SNPs are in the coding sequence, but do not change the amino acid sequence of the encoded polypeptide. Primers are designed to be positioned at positions 1071-1090 and positions 1379-1398 (underlined).

Figure 2
Coding sequence for bovine signal transducer and activator
of transcription (STAT1)

```
1    ctttaaatat agcctcaagt ttgccagtgg cttgcctgtg aaatagtgca aagctgtcct
61   gtatctgggc agaggataaa agttatgtgt gttattatat tttccacact ggccattgaa
121  aactaaagat tctctttctt gggagaatta gcttttggta tggctttatg atgctggcta
181  atatcaatag aaggaagtaa actttacaaa ttcatgagta gtatcttcca tttcagcttt
241  aataccaaag ttgaatatat tctgccttca tcatgaaatt gaagttagta aatgaaactg
301  tcttcacagt tctatcaagg gagccaaact attaacagct ctcttaaggc aaatcctatt
361  atttttcaa aaagttgaaa ttaattgtag atgtaaacaa actcagaaat ttaatgcatg
421  tttcataagt gggttcactt gtctttattg tttagtaaaa attttaaaat tgagaagaaa
481  aactagtaat tgacaaatca ttaggtggag attatgagaa tccaataatt tgaaaactca
541  tcctgtgtaa ctgccttgag aattgggtaa ttttcactgg caaatgtgta tctctcacaa
601  atacattaca gatggttcca ctaaaa
```

Notes: SNP is at position 213 (C/T), with C being the
nucleotide reported by the original submitter. Primers are
designed to be positioned at positions 11-31 and positions
306-325.

Figure 3
Partial genomic sequence of the region encoding bovine osteopontin (OPN/SPP1)

```
7561 taattaactc taaatattaa aattctcaca attaaagaac aaccactcca aaaaatagcc
7621 accaagcagg ccatttgggc tggttaaatg gatcttccct gcctgttggg cttccctgat
7681 agctcagttg gtaaagcatc tgcctgcaac ttggaagacc cgggttcagt ccctgggtcg
7741 ggaagactcc ctggagaagg aaatggcaac cccctctagt actcttgcct ggaaaatttc
7801 catggactga ggaccctggt aggctaagag tcagacagaa ctgagcaact tcacttcact
7861 ttcctgcctg tttgtaaaag tgagcttagg acaccaattg atctgtcagg ttgtcttccg
7921 gcttaatcct tccacaatga ggctagaaaa ataagacctg ctttggatgg aaacagctaa
7981 cttttgaata aaaaagttac gttgtatgat gtgcactgat ttgtgtcttt tcttcttcag
8041 aattctgtgt cctctgagga aactgatgac aacaaacaaa atgtgagtct ttgctttgat
8101 tctgatgtct gttgtgcctt agactcagga aggcactctt tctcctaatg acattgccca
8161 ggttcaaatt ccggcaaaat tccactagca aacccttcag gaactacttt ttattgggac
8221 tattaatagg gataagttaa atttgctttc cttaagattc tatttgaaga tgctgagaat
8281 ctataagaga agttagataa atgacccagg atatttgcaa atcagaagtg tgatagacat
8341 taactgagct atagtttcta cacatggata agagagtcac cttttgatta tccaggctaa
8401 tagggaggtg attttagttt tggggtgtg cattaataca tggattctct gatcccctga
8461 gaattttcat ttcaaataga aaggtagtc tcacaattat gtaēctgtat ttattggatc
8521 attgaaattt ggtaaattag tgtttattat gaacaaggaa aaacagtgtc attgatacaa
8581 atattataac tcatacgttt ggcttgaaa tatctgtgaa aatcgttttt atgagaaacc
8641 aagaaaaatg ccttagaata ggattccatt taccttgtg ttaaagggga aattggaata
8701 agctcatttt agcatttaaa agccattaag tgctttgttg tgaatacaaa gattctaaaa
8761 ctaaataaag atagtaaaat actaatgcac tgtaaagcct aagggacagt aaaaaccctg
8821 acacccattt ttctggccat cttgatttct agaccctccc aagtaagtcc aatgaaagcc
8881 ctgagcaaac agacgatcta gatgacgatg atgataacag ccaggacgtc aactctaatg
8941 actccgacga cgctgaaacc actgatgacc ctgaccattc cgacgagtct caccattctg
9001 atgaatctga tgaagttgat tttcccactg atattccaac aatcgcagtt ttcactccgt
9061 ttatccctac ggaaagcgca aatgatggcc gaggtgatag tgtggcttac ggactgaagt
```

Notes: SNP is at position 8514 (C/T), with C being the nucleotide reported by the original submitter. Primers are designed to be positioned at positions 8316-8338 and positions 8588-8606/7. Positions are numbered according to the GenBank.

Figure 4
Coding Sequence for bovine lectin-like oxidized LDL
receptor (OLR1)

```
   1   gcttcactct ctcattcttg gaatacattt gaaaatgact gttgatgacc ccaagggtat
  61   gaaagatcaa cttgatcaga agccaaatgg caagacagca aaaggttttg tttcctcttg
 121   gaggtggtac cctgctgctg tgactctagg ggtcctttgt ctgggattac tggtgactgt
 181   tatattgttg atactgcaat tatcccaggt ctctgatctc ataaagaaac agcaagcaaa
 241   tattactcac caggaagata tcctggaggg acagatttta gcccagcgcc gatcagaaaa
 301   atctgcccag gagtcacaga aggaactcaa agaaatgata gaaacccttg cccacaagct
 361   ggatgagaaa tccaagaaac taatggaact tcaccgccag aacctgaatc tccaagaagt
 421   tctgaaagag gcagcaaact attcaggtcc ttgtccccaa gactggctct ggcatgaaga
 481   aaactgttac caatttcct ctggctcttt taattgggaa aaaagccagg agaactgctt
 541   gtctttggat gcccacttgc tgaagattaa tagcacagat gaactggaat tcatccagca
 601   aatgattgcc cattccagtt tccccttctg gatggggttg tcaatgagga aacccaatta
 661   ctcgtggctt tgggaagatg gtactccttt gacgccccac ttgtttagaa ttcagggagc
 721   tgtttcccgt atgtatcctt cagggacctg tgcatatatt caaaggggaa ctgtttttgc
 781   tgaaaactgc attttaactg cattcagtat atgtcaaaag aaggcgaatc tattgagagc
 841   acagtgaatt tgaaggatct ggaggaaaag aaggaaacct ttgaattctc ttctggaatt
 901   taagctatac ttcatcactt agatgtaaac cattagagcc cagggaaatg cctgctactg
 961   gttgagtgca gaactcctta gcagagactg gcccagctgc ctggcaccct gatagcaaaa
1021   gttgcaattc cctctgtata tttttcccta acttgttcca agtcctcccc tgcaggactt
1081   cagagaagtc aatttttctg tttccattgt ttctaagaac ttgttgccta actcaaggtc
1141   acagcatttt tctcactttt gtcctatgct ttcttctagg cattgtagag ttttagattt
1201   tacatggaaa tctagaactt attttagatt aatttctaag tgatatatgg atgtatggaa
1261   gttttctgtt tgttttttgc ttgtgagtat tcaattgttt ttgcaacatt tgctgaaaag
1321   actattcttc cttcactaca ttgcctttgc actgttgtca acaattatcc atacatgcct
1381   ggctctattt ctggattttc tattcctttc catttattta tttattattc ttggcttaca
1441   acatcaccat gatatttga attctatggt tctttaatat atcttggaat cacatggtag
1501   tagttattca ttgttgttct tttttagagt tgtttggtta atctatgctt ttgtatttct
1561   gtcttaaatt ggcttgtcca tttctaaaaa aacttgaaat tttgaattgc actgaatcca
1621   tacataaatt tagggaaaat tgaattctta aaaatactga tttgttcaac tcatgaaaaa
1681   ggtgtattgc tctatttagg tattccttat tttctttaag caatgctttt taatgttctt
1741   tgtgtagata ttgttagatt atcatcatgt atttcacatt atttatgcta ctgtagatag
1801   tattgttatc atttgttgtt cttattttca aagtcttctg ctagtatgta gaattataat
1861   aaagtttgat attaatatt
```

Notes: SNP is at position 1070(C/A), with C being the
nucleotide reported by the original submitter. Primers are
designed to be positioned at positions 8316-8338 and
positions 821-1090.

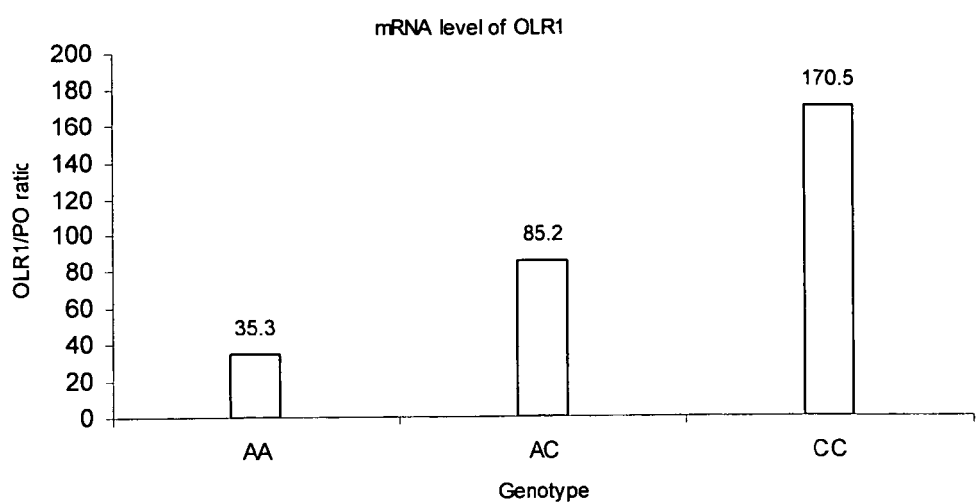
Fig. 5. Level of OLR1 mRNA in hearts from individuals with genotypes AA, AC, and CC at the 3' UTR SNP

SEQUENCE LISTING

<160> NUMBER OF SEQ ID NOS: 12

<210> SEQ ID NO 1
<211> LENGTH: 1463
<212> TYPE: DNA
<213> ORGANISM: Bos taurus

<400> SEQUENCE: 1

```
ggctggattg ccgcagaaat gtcccacggg agaatgaatc tggccctgtc tctggtcttc      60
atcctctgtg gcctgtttaa tagcatcttc tgtgaaaagc aacaacactc tcaaaagcac     120
atgaacctag tcttattaaa gaaaatttca gctctctccc agaagatgga agctcaccct     180
aaggattttg cccaagaatt gttcaaggct ttgataattg aggatcccag aaagaatatc     240
atcttctccc ccatggccat gaccaccacc ctggccaccc tctccctggg gatcaagtct     300
acaatgagaa cccaccaccc tgaggacctg aaacttgagc ccaaactgtt ggatgtgcac     360
aagtacttac agcctctggt ccacgtgggg cgtgagctag tgaagcagaa ggtactgaag     420
caccagcaca ttctctttat caacagaaaa atgatggtca accagatgct tctacagcag     480
ataagcaagc tgcagggaat ggacatccag atgattgact ttacagatat agaaaaagcc     540
aagaagacca tcagccacca tgtggctgaa aaaacacata cgaaaatcac aaacttaatc     600
accgacctga accctgagac catcctgtgt cttgttaacc acattttctt caaaggcatc     660
ttgaaaagag cttttcagcc caaactcacc cagaaggagg tcttctttgt gaatgaccaa     720
accaaagtgc aggtggacat gatgagaaag acagaacgga tgctttacag ccggtcagag     780
gagctacatg ctacgatggt taagatgcct tgcaaaggaa atgtgtccct aactctcatg     840
cttccagatg ccggacaatt tgacactgat cttaaaaaga tgactgctaa gcagctaaa      900
cttcagaaaa tcagtgactt cagactggtg cgcttaattt tgcccaagtt gaagatctcc     960
ttcaagataa actttaagca tctgcttccc aagattgacc ccaaacatat actgactgcc    1020
acagcaatct cacaggccat cacatcgaag gctcccctgc ctaatttgga ggccctacat    1080
caagctgaga tagagctgag cgagcacgcc ttaaccgtgg acacagccat tcacacagat    1140
aatctgttga aagtcccagt gaaggcaaag gaggtcccgg cggtcgtgaa agtcccaatg    1200
aaggcaaagg aggtcccggc ggtcgtgaaa gtcccaatga acacaaagga ggtcccagtg    1260
gtcgtgaaag tcccaatgaa cacaaaggag gtcccagtgg tcgtgaaggt caacagaccc    1320
ttcttgctgt ttgtggagga tgagaagact caaagagacc tctttgtggg caaagtcctc    1380
aaccccaag ttgagtagag ccagggccac actgtgcagc acaggaactt agcaggccat     1440
gaataaaaag agtacaattc acc                                            1463
```

<210> SEQ ID NO 2
<211> LENGTH: 626
<212> TYPE: DNA
<213> ORGANISM: Bos taurus

<400> SEQUENCE: 2

```
ctttaaatat agcctcaagt ttgccagtgg cttgcctgtg aaatagtgca aagctgtcct      60
gtatctgggc agaggataaa agttatgtgt gttattatat tttccacact ggccattgaa     120
aactaaagat tctctttctt gggagaatta gcttttggta tggctttatg atgctggcta     180
atatcaatag aaggaagtaa actttacaaa ttcatgagta gtatcttcca tttcagcttt     240
aataccaaag ttgaatatat tctgccttca tcatgaaatt gaagttagta aatgaaactg     300
```

| | |
|---|---|
| tcttcacagt tctatcaagg gagccaaact attaacagct ctcttaaggc aaatcctatt | 360 |
| atttttcaa aaagttgaaa ttaattgtag atgtaaacaa actcagaaat ttaatgcatg | 420 |
| tttcataagt gggttcactt gtctttattg tttagtaaaa attttaaaat tgagaagaaa | 480 |
| aactagtaat tgacaaatca ttaggtggag attatgagaa tccaataatt tgaaaactca | 540 |
| tcctgtgtaa ctgccttgag aattgggtaa ttttcactgg caaatgtgta tctctcacaa | 600 |
| atacattaca gatggttcca ctaaaa | 626 |

<210> SEQ ID NO 3
<211> LENGTH: 1560
<212> TYPE: DNA
<213> ORGANISM: Bos taurus

<400> SEQUENCE: 3

| | |
|---|---|
| taattaactc taaatattaa aattctcaca attaaagaac aaccactcca aaaaatagcc | 60 |
| accaagcagg ccatttgggc tggttaaatg gatcttccct gcctgttggg cttccctgat | 120 |
| agctcagttg gtaaagcatc tgcctgcaac ttggaagacc cgggttcagt ccctgggtcg | 180 |
| ggaagactcc ctggagaagg aaatggcaac cccctctagt actcttgcct ggaaaatttc | 240 |
| catggactga ggaccctggt aggctaagag tcagacagaa ctgagcaact tcacttcact | 300 |
| ttcctgcctg tttgtaaaag tgagcttagg acaccaattg atctgtcagg ttgtcttccg | 360 |
| gcttaatcct tccacaatga ggctagaaaa ataagacctg ctttggatgg aaacagctaa | 420 |
| cttttgaata aaaagttac gttgtatgat gtgcactgat ttgtgtcttt tcttcttcag | 480 |
| aattctgtgt cctctgagga aactgatgac aacaaacaaa atgtgagtct ttgctttgat | 540 |
| tctgatgtct gttgtgcctt agactcagga aggcactctt tctcctaatg acattgccca | 600 |
| ggttcaaatt ccggcaaaat tccactagca aacccttcag gaactacttt ttattgggac | 660 |
| tattaatagg gataagttaa atttgctttc cttaagattc tatttgaaga tgctgagaat | 720 |
| ctataagaga agttagataa atgacccagg atatttgcaa atcagaagtg tgatagacat | 780 |
| taactgagct atagtttcta cacatggata agagagtcac cttttgatta tccaggctaa | 840 |
| tagggaggtg attttagttt tgggggtgtg cattaataca tggattctct gatccctga | 900 |
| gaattttcat ttcaaataga aaaggtagtc tcacaattat gtatctgtat ttattggatc | 960 |
| attgaaattt ggtaaattag tgtttattat gaacaaggaa aaacagtgtc attgatacaa | 1020 |
| atattataac tcatacgttt ggcttgaaaa tatctgtgaa atcgttttt atgagaaacc | 1080 |
| aagaaaaatg cctagaata ggattccatt taccccttgtg ttaaagggga aattggaata | 1140 |
| agctcatttt agcatttaaa agccattaag tgctttgttg tgaatacaaa gattctaaaa | 1200 |
| ctaaataaag atagtaaaat actaatgcac tgtaaagcct aagggacagt aaaaaccctg | 1260 |
| acacccattt ttctggccat cttgatttct agaccctccc aagtaagtcc aatgaaagcc | 1320 |
| ctgagcaaac agacgatcta gatgacgatg atgataacag ccaggacgtc aactctaatg | 1380 |
| actccgacga cgctgaaacc actgatgacc ctgaccattc cgacgagtct caccattctg | 1440 |
| atgaatctga tgaagttgat tttcccactg atattccaac aatcgcagtt ttcactccgt | 1500 |
| ttatccctac ggaaagcgca aatgatggcc gaggtgatag tgtggcttac ggactgaagt | 1560 |

<210> SEQ ID NO 4
<211> LENGTH: 1879
<212> TYPE: DNA
<213> ORGANISM: Bos taurus

<400> SEQUENCE: 4

-continued

```
gcttcactct ctcattcttg gaatacattt gaaaatgact gttgatgacc ccaagggtat      60
gaaagatcaa cttgatcaga agccaaatgg caagacagca aaaggttttg tttcctcttg     120
gaggtggtac cctgctgctg tgactctagg ggtcctttgt ctgggattac tggtgactgt     180
tatattgttg atactgcaat tatcccaggt ctctgatctc ataaagaaac agcaagcaaa     240
tattactcac caggaagata tcctggaggg acagatttta gcccagcgcc gatcagaaaa     300
atctgcccag gagtcacaga aggaactcaa agaaatgata gaaacccttg cccacaagct     360
ggatgagaaa tccaagaaac taatggaact tcaccgccag aacctgaatc tccaagaagt     420
tctgaaagag gcagcaaact attcaggtcc ttgtccccaa gactggctct ggcatgaaga     480
aaactgttac caattttcct ctggctcttt taattgggaa aaaagccagg agaactgctt     540
gtctttggat gcccacttgc tgaagattaa tagcacagat gaactggaat tcatccagca     600
aatgattgcc cattccagtt tccccttctg gatggggttg tcaatgagga aacccaatta     660
ctcgtggctt tgggaagatg gtactccttt gacgccccac ttgtttagaa ttcagggagc     720
tgtttcccgt atgtatcctt cagggacctg tgcatatatt caaaggggaa ctgttttgc      780
tgaaaactgc atttaactg cattcagtat atgtcaaaag aaggcgaatc tattgagagc      840
acagtgaatt tgaaggatct ggaggaaaag aaggaaacct ttgaattctc ttctggaatt     900
taagctatac ttcatcactt agatgtaaac cattagagcc cagggaaatg cctgctactg     960
gttgagtgca gaactcctta gcagagactg gcccagctgc ctggcacctt gatagcaaaa    1020
gttgcaattc cctctgtata ttttttccta acttgttcca agtcctcccc tgcaggactt    1080
cagagaagtc aattttctg tttccattgt ttctaagaac ttgttgccta actcaaggtc     1140
acagcatttt tctcactttt gtcctatgct ttcttctagg cattgtagag ttttagattt    1200
tacatggaaa tctagaactt attttagatt aatttctaag tgatatatgg atgtatggaa    1260
gttttctgtt tgtttttttgc ttgtgagtat tcaattgttt ttgcaacatt tgctgaaaag   1320
actattcttc cttcactaca ttgcctttgc actgttgtca acaattatcc atacatgcct    1380
ggctctattt ctggatttc tattcctttc catttattta tttattattc ttggcttaca    1440
acatcaccat gatattttga attctatggt tctttaatat atcttggaat cacatggtag    1500
tagttattca ttgttgttct tttttagagt tgtttggtta atctatgctt ttgtatttct    1560
gtcttaaatt ggcttgtcca tttctaaaaa aacttgaaat tttgaattgc actgaatcca    1620
tacataaatt tagggaaaat tgaattctta aaaatactga tttgttcaac tcatgaaaaa    1680
ggtgtattgc tctatttagg tattccttat tttctttaag caatgctttt taatgttctt    1740
tgtgtagata ttgttagatt atcatcatgt atttcacatt atttatgcta ctgtagatag    1800
tattgttatc atttgttgtt cttatttca aagtcttctg ctagtatgta gaattataat     1860
aaagtttgat attaatatt                                                 1879
```

<210> SEQ ID NO 5
<211> LENGTH: 20
<212> TYPE: DNA
<213> ORGANISM: Artificial
<220> FEATURE:
<223> OTHER INFORMATION: Oligonucleotide primer

<400> SEQUENCE: 5

```
gcctcaagtt tgccagtggc                                                  20
```

<210> SEQ ID NO 6
<211> LENGTH: 20
<212> TYPE: DNA

```
<213> ORGANISM: Artificial
<220> FEATURE:
<223> OTHER INFORMATION: Oligonucleotide primer

<400> SEQUENCE: 6
ggctcccttg atagaactgt                                              20

<210> SEQ ID NO 7
<211> LENGTH: 22
<212> TYPE: DNA
<213> ORGANISM: Artificial
<220> FEATURE:
<223> OTHER INFORMATION: oligonucleotide primer

<400> SEQUENCE: 7
gcaaatcaga agtgtgatag ac                                           22

<210> SEQ ID NO 8
<211> LENGTH: 20
<212> TYPE: DNA
<213> ORGANISM: Artificial
<220> FEATURE:
<223> OTHER INFORMATION: Oligonucleotide primer

<400> SEQUENCE: 8
ccaagccaaa cgtatgagtt                                              20

<210> SEQ ID NO 9
<211> LENGTH: 21
<212> TYPE: DNA
<213> ORGANISM: Artificial
<220> FEATURE:
<223> OTHER INFORMATION: Oligonucleotide primer

<400> SEQUENCE: 9
atgactgttg atgaccccaa g                                            21

<210> SEQ ID NO 10
<211> LENGTH: 26
<212> TYPE: DNA
<213> ORGANISM: Artificial
<220> FEATURE:
<223> OTHER INFORMATION: Oligonucleotide primer

<400> SEQUENCE: 10
cactgtgctc tcaatagatt cgcctt                                       26

<210> SEQ ID NO 11
<211> LENGTH: 20
<212> TYPE: DNA
<213> ORGANISM: Artificial
<220> FEATURE:
<223> OTHER INFORMATION: Oligonucleotide primer

<400> SEQUENCE: 11
aaggcgaatc tattgagagc                                              20

<210> SEQ ID NO 12
<211> LENGTH: 19
<212> TYPE: DNA
<213> ORGANISM: Artificial
<220> FEATURE:
<223> OTHER INFORMATION: Oligonucleotide primer

<400> SEQUENCE: 12
acttctctga agtcctgca                                               19
```

DAIRY CATTLE BREEDING FOR IMPROVED MILK PRODUCTION TRAITS IN CATTLE

FEDERAL GOVERNMENT INTERESTS

This invention was made partially with United States government support awarded by USDA/CSREES, under the grant number 05-CRHF-0-6055. The United States may have certain rights in this application.

FIELD OF THE INVENTION

The present invention relates to a method of cattle progeny testing using molecular genetic methods by assaying for the presence of at least one genetic marker which is indicative of improved milk production and reproduction traits, including milk yield and milk composition such milk fat content and milk protein content, somatic cell score, and productive life.

BACKGROUND OF THE INVENTION

Dairy cows are significant investments for dairy farmers, and enormous efforts, such as systematic animal breeding programs and artificial insemination, have been and continue to be invested in ensuring that the animals have high and sustained productivity, and that the milk produced is of high quality or has desired composition. A successful breeding family is the Holstein line derived from Carlin-M Ivenhoe Bell. More than 25% of the highest total performance index Holstein bulls in the United States are progenies of this individual.

Traditional breeding techniques involve the studying of sire progenies, and evaluating their milk production ratings (transmitting abilities) to guide further breeding. This standard technique requires years to evaluate the true genetic value by progeny testing each bull. Many cows must be bred and give birth to offspring. The females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of environmental and developmental variants. There is thus a need for a method of genetically evaluating cattle to enable breeders to more accurately select animals at both the phenotypic and the genetic level.

Marker-assisted selection can lower the high cost and reduce the extended time commitment of progeny testing currently used to improve sires, since young bull progeny could be evaluated immediately after birth or even prior to birth for the presence/absence of the marker, and young bulls that are determined by genetic testing to have undesirable markers would never be progeny tested. Therefore, there is also a need for genetic markers for improved milk production traits.

SUMMARY OF THE INVENTION

It has been surprisingly discovered that dairy cattle whose genome has a certain genotype, specifically a single nucleotide polymorphism (SNP) exhibits highly desirable milk production traits. Specifically, (1) a cow whose bovine uterine milk protein (UTMP) coding sequence (FIG. 1; SEQ ID NO: 1) has a guanine at position 1296 (SNP1) produces milk with increased milk fat; (2) a cow whose signal transducer and activator of transcription (STAT1) coding sequence (FIG. 2; SEQ ID NO: 2) has a cytosine base at position 213 (SNP2) produces milk with increased milk fat yield, increased milk fat percentage, increased milk protein percentage. The thymine at position 213 is associated with a decrease in somatic cell score (SCS) versus the cytosine allele (3) a cow whose genomic sequence for the osteopontin (OPN) gene (see FIG. 3; SEQ ID NO: 3) has a cytosine base at position 8514 (SNP3) produces milk with increased milk protein percentage, and (4) a cow whose lectin-like oxidized LDL receptor (OLR1) coding sequence (FIG. 4; SEQ ID NO: 4) has an cytosine base at position 1070 (SNP4) produces milk with increased milk fat yield, increased milk fat percentage, and increased productive life.

The present invention provides an isolated nucleic acid molecule comprising a polymorphic site at position 1296 of FIG. 1 (SEQ ID NO: 1) and at least 15 contiguous nucleotides of the SEQ ID NO: 1 adjacent to the polymorphic site; an isolated nucleic acid molecule comprising a polymorphic site at position 213 of FIG. 2 (SEQ ID NO: 2) and at least 15 contiguous nucleotides of the SEQ ID NO: 2 adjacent to the polymorphic site; an isolated nucleic acid molecule comprising a polymorphic site at position 8514 of FIG. 3 (SEQ ID NO: 3) and at least 15 contiguous nucleotides of the SEQ ID NO: 3 adjacent to the polymorphic site; and an isolated nucleic acid molecule comprising a polymorphic site at position 1070 of FIG. 4 (SEQ ID NO: 4) and at least 15 contiguous bases of the SEQ ID NO: 1 adjacent to the polymorphic site.

Preferably, the nucleic acid molecule comprises i) a guanine base at position 1296 of SEQ ID NO: 1; ii) a cytosine base at position 213 of SEQ ID NO: 2; iii) a cytosine base at position 8514 of FIG. 3; or iv) a cytosine base at position 1070 of SEQ ID NO: 4.

Preferably, the nucleic acid molecule which comprises at least 17, more preferably at least 20, still more preferably at least 25, contiguous nucleotides of the respective sequences adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is near the 3'-end of the nucleic acid molecule. In another embodiment, the nucleic acid molecule contains the polymorphic site which is at the 3'-end of the nucleic acid molecule.

The present invention also provides an array of nucleic acid molecules comprising at least one of the nucleic acid molecules described above.

The present invention further provides a kit comprising the above-described nucleic acid molecule, and a suitable container. The kit preferably contains reagents useful for nucleotide amplification or detection.

Also provided is a method for detecting single nucleotide polymorphism (SNP) in a bovine polynucleotide comprising or coding for a sequence selected from the group consisting of SEQ ID NOs: 1, 2, 3 and 4, the method comprising determining the identity of a nucleotide at the respective polymorphic site of SEQ ID NOs: 1, 2, 3 or 4, and comparing the identity to the nucleotide at a corresponding position of the sequences respectively depicted in FIGS. 1, 2, 3 and 4.

In another embodiment, the present invention provides a method for genotyping a bovine cell, comprising determining the identity of at least one of the polymorphic sites described above. Suitable bovine cell may be an adult cell, an embryo cell, a sperm, an egg, a fertilized egg, or a zygote. The identity of the nucleotide may be determined by sequencing the aforementioned genes, or a relevant fragment thereof, isolated from the cell. The relevant gene or nucleic acid fragment may be isolated from a sample containing the cell via amplification by the polymerase chain reaction (PCR) of genomic DNA of the cell, or by RT-PCR of the mRNA of the cell. Preferably, the PCR or RT-PCR is conducted with a suitable pair of primers depicted in FIGS. 1, 2, 3 or 4.

In a further embodiment, the present invention provides a method for progeny testing of cattle, the method comprising collecting a nucleic acid sample from the progeny, and genotyping the nucleic sample as described above.

Further provided is a method for selectively breeding of cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo, and optionally terminating pregnancy if said developing embryo is not a genotype having the desired SNP at one or more of the polymorphic positions described above.

In a preferred embodiment, the method is used for selectively breeding dairy cattle, comprising selecting a bull that has one or more of the desired genotype identified in the present invention and using its semen for fertilizing a female animal. More preferably, the female animal also has the desired genotype. Preferably, the male and female parents for the breeding program are homozygous with regard to the desired SNP allele. MOET procedure may be preferably used for the selective breeding.

The present invention also provides a method for testing dairy cattle for its milk production traits, comprising genotyping its cells, wherein cattle having a desired genotype indicates that the cattle has desirable milk production traits.

BRIEF DESCRIPTION OF THE DRAWINGS

FIG. 1 shows the coding sequence for bovine uterine milk protein (UTMP) (GenBank Accession No. L22095) (SEQ ID NO: 1), as well as the sequences and locations of the primers used in Example 1.

FIG. 2 shows the coding sequence for bovine signal transducer and activator of transcription protein (STAT1) (GenBank Accession No. AW289395) (SEQ ID NO: 2), as well as the sequences and locations of the primers used in Example 2.

FIG. 3 shows the partial genomic sequence of the region encoding bovine osteopontin (OPN/SPP1) (GenBank Accession No. NW_255516) (SEQ ID NO: 3), as well as the sequences and locations of the primers used in Example 3.

FIG. 4 shows the coding sequence for bovine lectin-like oxidized LDL receptor (OLR1) (GenBank Accession No. D89049)(SEQ ID NO: 4), as well as the sequences and locations of the primers used in Example 4.

FIG. 5 shows a within-sire-family analysis for milk protein percentage in 14 heterozygous-sire families and 14 homozygous-sire families. The estimate of the effect of genotypes CC and CT on milk protein percentage was higher than the effect of the TT genotype in 17 families.

DETAILED DESCRIPTION OF THE INVENTION

The present inventor has identified four single nucleotide polymorphisms (SNPs) that are associated with improved milk production traits in dairy cattle. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker.

Details of the four SNPs of the present invention are described in Table 1.

TABLE 1

Summary of SNPs Associated with Improved Milk Production Traits

| Gene/Locus | Accession number | SNP and position | Trait associated | Significance of the gene (P) |
|---|---|---|---|---|
| Bovine Uterine milk protein (UTMP) | L22095 | (1296; A/G) | Milk fat percentage | 0.0423 |
| Signal transducer and activator of transcription (STAT1) | AW289395 | (213; C/T) C-allele T-allele | Milk fat percentage Milk protein percentage Somatic cell score | 0.031 0.0423 0.0527 |
| Osteopontin (OPN/SPP1) | NW_255516 | 8514 (C/T) | Milk protein percentage Milk fat percentage | 0.0255 0.048 |
| OLR1 | D89049 | (1070; C/A) | Milk fat yield Milk fat percentage | 0.00058 0.00001 |

The present invention also encompasses the complementary sequence corresponding to any of the provided polymorphisms. In order to provide an unambiguous identification of the specific site of a polymorphism, the numbering of the original sequences in the GenBank is shown and is used.

The present invention provides nucleic acid based genetic markers for identifying bovine animals with superior reproduction and milk production traits. In general, for use as markers, nucleic acid fragments, preferably DNA fragments, will be of at least 10 to 12 nucleotides (nt), preferably at least 15 nt, usually at least 20 nt, often at least 50 nt. Such small DNA fragments are useful as primers for the polymerase chain reaction (PCR), and probes for hybridization screening, for use on a microarray etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at position 1296 of the bovine uterine milk protein (UTMP) coding sequence (FIG. 1; SEQ ID NO: 1) is guanine. An oligonucleotide probe can be used for such purpose. Preferably, the oligonucleotide probe will have a detectable label, and contain a cytosine (C) at the corresponding position. Experimental conditions can be chosen such that if the sample DNA contains an C, then the hybridization signal can be detected because the probe hybridizes to the corresponding complementary DNA strand in the sample, while if the sample DNA contains an A, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the genes. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms, and may include all or a subset of the polymorphisms listed in Table 1.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism at position 1296 of the UTMP gene may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide is described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the relevant genetic locus of the sample of interest may be amplified via PCR and directly sequenced, and the sequence be compared to the information of Table 1. In this case, two sets of PCR primers are preferably used for optimal amplification and to avoid the need to sequence an unnecessarily long fragment. Four such pairs of primers are depicted in FIGS. 1-4, respectively. It is readily recognized that numerous other primers can be devised to achieve the same objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers of the present invention.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses at least one of the SNPs of the present invention, which are indicative of improved milk production traits.

Further provided is a method for genotyping the bovine UTMP, STAT1, OPN, and OLR1 genes, comprising determining the nucleotide identity for the two copies of the genetic loci. One embodiment of a genotyping method of the invention involves examining both copies of the genes or coding sequences listed in Table 1, or a fragment thereof, to identify the nucleotide pair at one or more polymorphic sites listed in Table 1 in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at each of the polymorphic site listed in Table 1.

The present invention further provides a kit for detecting the SNPs of the present invention or for genotyping a bovine sample, the kit comprising in a container a nucleic acid molecule, as described above, designed for detecting the one or more of the polymorphisms listed in Table 1, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected for or removed from the breeding program. Preferably, individuals carrying at least one of SNPs 1, 2, 3 or 4 are selected. Preferably, these individuals are homozygous with regard to the SNP. For example, the individual is homozygous with regard to position 1296 (SNP1) of the UTMP gene and has a G at the position, or homozygous with regard to position 213 of the STAT1 coding sequence and has a C at the position, or homozygous with regard to position 8514 of the OPN gene and has a C at the position, or homozygous with regard to position 1070 of the OLR1 coding sequence and has a C at the position.

The following examples are intended to illustrate preferred embodiments of the invention and should not be interpreted to limit the scope of the invention as defined in the claims.

EXAMPLES

Example 1

Association of the UMP Gene with Milk Production Traits in Holstein Dairy Cattle The UTMP gene was chosen because of previous linkage mapping studies indicating the presence of gene(s) affecting milk production traits. Sequencing of the UTMP gene revealed an A/G single nucleotide polymorphism (SNP). The association between A/G alleles and milk production and health traits was tested in 1509 DNA samples obtained from the Cooperative Dairy DNA Repository. The G allele was found to be strongly associated with increased milk fat percentage (P=0.423). The expression of the UTMP is controlled by progesterone and first synthesized in the uterine glands. UTMP has important functions in initiation of pregnancy by inhibiting proliferation of lymphocytes and natural killer cells. Possible roles of UTMP include nutrition of the conceptus, growth control, and immunosuppresion of the local maternal system. Thus, although milk fat percentage, at present, is the only trait that shows significant association with the gene, the functions of this gene suggest other important associations that might be uncovered in the near future. It is noteworthy that the G allele did not show any significant unfavorable effect on any of the examined traits (productive life, SCS, milk composition and yield).

Example 2

Effects of the Bovine STAT1 Variants on Production and Health Traits in Dairy Cattle Signal transducers and activators of transcription (STAT) factors are a family of cytoplasmic proteins that are activated by interaction with cytokines, growth factors, and hormones (Darnell 1997). The STAT proteins are activated via a cascade of phosphorylation events in which janus protein tyrosine kinases (JAKs) are first phosphorylated. STATs, in turn, become phosphorylated and they detach from the receptor complex. Then homo- or heterodimers of STATs translocate from the cytoplasm to the nucleus where they interact with promoter regions and regulate gene expression (Darnell 1997).

There is some evidence that STAT1 is involved in the development and differentiation of mammary gland. Boutinaud and Jammes (2004) measured the expression levels of STAT1, STAT3, and STAT5 in the mammary gland of lactating goats and found that the expression of these genes is regulated by growth hormone. Stewart et al. (1999) studied the regulation of STAT expression by effectors of adipocyte differentiation. They found that STAT1, STAT5A, and STAT5B are not exclusively regulated by individual effectors of differentiation, but their expression tightly correlates with lipid accumulation. Studies on the expression of STATs in different tissues and at different developmental stages have shown that STAT1 and STAT3 are constitutively expressed at constant levels through pregnancy, lactation, and involution while STAT4 and STAT5 are developmentally regulated (Watson 2001).

The bovine STAT1 maps to chromosome 2 at interval 60-63 cM (Band et al. 2000). Different whole genome scans have reported significant associations between production traits and microsatellite markers in the vicinity of STAT1. Mosig et al. (2001) reported a putative QTL affecting milk protein percentage in linkage with microsatellite marker BMS1126 at position 61.7 cM from the centromere. In addition, Ashwell et al. (2004) reported a QTL affecting milk fat percentage in linkage with microsatellites ETH121 and BM4440 at interval 38.0-60.3 cM. Also, Ron et al. (2004) reported a QTL affecting milk protein percentage at interval 61.7-70 cM from the centromere. These QTL studies, along with the studies on the function, involvement, and expression of STAT1 in mammary gland, prompted us to investigate the effects of this gene on production traits in dairy cattle.

By direct sequencing of genomic DNA, a single nucleotide polymorphism (SNP) in the EST corresponding to STAT1 (GenBank accession number AW289395) at position 213 was identified. Semen samples from 29 Holstein sires and their 1292 sons (average of 46 sons per sire) were obtained from the Cooperative Dairy DNA Repository, which is maintained by the USDA Bovine Functional Genomics Laboratory. Daughter yield deviations (DYD) data for milk yield, milk protein and fat yields, milk protein and fat percentages, and somatic cell score (SCS) were obtained from the Animal Improvement Programs Laboratory. The primers STATF: 5'-GCCTCAAGTTTGCCAGTGGC-3' (SEQ ID NO: 5) and STATR: 5'-GGCTCCCTTGATAGAACTGT-3' (SEQ ID NO: 6) were designed to amplify a fragment of 314 bp of genomic DNA. Amplification of genomic DNA was performed in 25 µl of reaction volume, which included 50 ng of genomic DNA, 50 ng of each primer, 200 µM of each dNTP, 2.5 µl of 10×PCR buffer (Promega, Madison, Wis.), and 0.3 units of Taq DNA polymerase (Promega). The temperature cycles were as follows: 95° C. for min; 32 cycles of 94° C. for 45 s, touchdown annealing from 65° C.-53° C. for 45 s (−2° C./cycle), 72° C. for 45 s; and a final extension at 72° C. for 7 min.

The PCR products were digested with the restriction enzyme PagI that distinguishes alleles C and T of the SNP. The digestion products were electrophoresed on a 1.5% agarose gel; the T allele (uncut) was indicated by a band of 314 bp and the C allele was indicated by two bands of 201 and 113 bp. Weighted least squares analysis was employed to study the effects of STAT1 variants on production and functional traits. The model used was $$y_{ij}=\mu+sire_i+bx_{ij}+e_{ij}$$

where $y_{ij}$ is the DYD of the trait that was considered for son j of sire i, $sire_i$ is the fixed effect of sire i, b is the regression coefficient representing half of the gene substitution effect (Falconer and Mackey 1996), $x_{ij}$ is the number of C alleles (0, 1, or 2), and $e_{ij}$ is the residual. Reliability of the son's DYD was incorporated into the model to obtain weighted least squares estimates for the allele effects.

The analysis found a significant effect of STAT1 variants on milk fat percentage (P=0.0331), on milk protein percentage (P=0.0423), and on SCS (P=0.0527) in across family analysis (Table 2). The estimate of the increase in milk fat percentage of the C allele was 0.01%. The C allele was also associated with an increase in milk protein percentage versus the T allele (Table 2). Also, the T allele was associated with an increase in SCS versus the C allele.

TABLE 2

Estimated allele substitution effects (α/2) of the STAT1 C allele and standard error (SE) for milk production and health traits

| Trait | α/2(SE) | P |
|---|---|---|
| Milk Fat yield | 1.76 (1.07) | 0.1011 |
| Milk fat percentage | 0.01 (0.004) | 0.0311 |
| Milk yield | 19.5 (29.7) | 0.5101 |
| Milk protein percentage | 0.004 (0.002) | 0.0423 |
| Milk protein yield | 0.51 (0.73) | 0.4888 |
| SCS | 0.019 (0.01) | 0.0527 |

The observed effects of the bovine STAT1 on milk composition and SCS traits was not surprising because of the following reasons:

1. The expression of STAT1 is under the control of the hormone prolactin. Following binding of prolactin to its receptor, a cascade of events is initiated that leads to activation of the STAT1, STAT3, and STAT5 proteins which in turn regulate the transcription of genes involved in secretion of milk proteins and components (Tucker 2000; Bole-Feysot et al. 2005).

2. Results in this example show that STAT1 was associated with milk fat and protein percentages. There is some evidence that STATs might be important for the regulation of fat metabolism and milk protein synthesis probably through the prolactin signal transduction pathway operating in the mammary gland (Mao et al. 2002).

3. Interferons regulate cellular antiviral, antiproliferative, and immunological responses. STAT1 has been shown to be essential for cell growth suppression in response to interferon-γ (Akira 1999). Moreover, it was reported that Stat1-deficient mice were found to be highly sensitive to infection by pathogens and they develop tumors more frequently than normal mice (Akira 1999; Watson 2001). These studies strongly indicate that STAT1 might have some roles in the immune response. The results in this example on the effect of STAT1 on somatic cells in milk, indicator for health in cows, are consistent with reported functions of this gene in the immune response of human and mouse.

Recently, the positional comparative candidate gene analysis and previous quantitative trait loci linkage mapping results were used to search for candidate genes affecting milk production traits, and a significant association between different haplotypes of the protease inhibitor gene and several production traits in Holstein dairy cattle including milk yield, milk fat yield, and SCS was found (Khatib et al. 2005). Using this approach STAT1 was chosen as a candidate gene affecting milk production traits References for Example 2

Akira S. (1999). Functional roles of STAT family proteins: lessons from knockout mice. *Stem Cells* 17, 138-46. 141

Ashwell M. S., Heyen D. W., Sonstegard T. S. et al. (2004). Detection of quantitative trait loci affecting milk production, health, and reproductive traits in Holstein cattle. *Journal of Dairy Science* 87, 468-75.

Band M. R., Larson J. H., Rebeiz M. et al. (2000). An ordered comparative map of the cattle and human genomes. *Genome Research* 10, 1359-68.

Bole-Feysot C., Goffin V., Edery M. et al. (2005). Prolactin (PRL) and its receptor: actions, signal transduction pathways and phenotypes observed in PRL receptor knockout mice. *Endocrine Reviews* 19, 225-68.

Boutinaud M. & Jammes H. (2004). Growth hormone increases StatS and Stat1 expression in lactating goat mammary gland: a specific effect compared to milking frequency. *Domistic Snimal Endocrinology* 27, 363-78.

Darnell J. E. (1997). STATs and gene regulation. *Science* 277, 1630-5.

Falconer D. & Mackay T. F. (1996). Quantitative genetics. 4th ed. Addison Wesley Longman Ltd., Essex, England.

Khatib H., Heifetz E. & Dekkers J. C. (2005). Association of the protease inhibitor gene with production traits in Holstein dairy cattle. *Journal of Dairy Science* 88, 1208-13.

Mao J., Molenaar A. J., Wheeler T. T. & Seyfert H. M. (2002). STAT5 binding contributes to lactational stimulation of promoter III expressing the bovine acetyl-CoA carboxylase alpha-encoding gene in the mammary gland. *Journal of Molecular Endocrinology* 29, 73-88.

Mosig M. O., Lipkin E., Khutoreskaya G. et al. (2001). A whole genome scan for quantitative trait loci affecting milk protein percentage in Israeli-Holstein cattle, by means of selective milk DNA pooling in a daughter design, using an adjusted false discovery rate criterion. *Genetics* 157, 1683-98.

Ron M., Feldmesser E., Golik M. et al. (2004). A complete genome scan of the Israeli Holstein population for quantitative trait loci by a daughter design. *Journal of Dairy Science* 87, 476-90.

Stewart W. C., Morrison R. F., Young S. L. et al. (1999). Regulation of signal transducers and activators of transcription (STATs) by effectors of adipogenesis: coordinate regulation of STATs 1, 5A, and 5B with peroxisome proliferator-activated receptor—gamma and C/AAAT enhancer binding protein-alpha *Biochimica et Biophysica Acta* 1452, 188-96.

Tucker H. A. (2000). Hormones, mammary growth, and lactation: a 41-year perspective. *Journal of Dairy Science* 83, 874-84.

Watson C. J. (2001). Stat transcription factors in mammary gland development and tumorigenesis. *Journal of Mammary Gland Biology and Neoplasia* 6, 115-27.

Example 3

Association of the Osteopontin Gene with Milk Protein Percentage in Dairy Cattle Osteopontin (OPN) is a highly phosphorylated glycoprotein whose gene has been cloned and sequenced in different species. Comparative sequence analysis of bovine OPN cDNA with various species has revealed both conserved and non-conserved sequences (Kerr et al. 1991). It was found, for example, that the bovine and ovine sequences have a 22 amino acid gap compared to all other examined species. Bovine OPN consists of six exons spanning about 7 kb of genomic DNA (Accession number NW_255516) and encodes a 278 amino acid protein (Kerr et al. 1991). Since its first description in 1979 as a protein associated with malignant transformation, OPN has been intensively studied in human, mouse, and sheep. It has been suggested that human OPN has various roles in cell adhesion, chemotaxis, cell survival, tissue remodeling, regulation of inflammation, fetal growth and development, and in initiating and maintaining pregnancy (Denhardt et al. 2001; Johnson et al. 2003).

Constitutive expression of OPN exists in several tissues, and the protein is present in milk, plasma, and urine. The OPN concentration in human milk ranges from 3 to 10 µg/ml (Senger et al. 1989). Using microarray analysis of RNA from human milk cells, Nagatomo et al. (2004) found that OPN showed the highest expression among 240 genes examined. They also found that both mRNA and protein levels were highly expressed throughout the entire lactation. The presence of OPN in milk and the high expression in mammary gland epithelial cells may account for the proliferation and differentiation of mammary glands (Nagatomo et al. 2004). The major sources of OPN were mammary gland epithelial cells and monocytes and macrophages in milk. OPN has also been detected in raw milk of cows at a concentration of 8 mg/L (Bayless et al. 1997). This has prompted us to investigate the effects of OPN on milk production traits in dairy cattle.

Previously, several whole genome scans have identified QTL affecting milk production traits on bovine chromosome 6 close to the OPN location (Zhang et al. 1998; Mosig et al. 2001; Ron et al. 2001; Nadesalingam et al. 2001; Rodriguez-Zas et al. 2002; Ashwell et al. 2004; Olsen et al. 2004). Ron and colleagues (2001) localized a QTL affecting protein percentage to a confidence interval of 4 cM in the region of OPN. Based on the aforementioned studies on the expression of OPN in the mammary gland and milk production QTL in the vicinity of the gene, possible associations between variants of the gene and milk production traits in Holstein dairy cattle were investigated.

Materials and Methods

Data Semen samples from 28 Holstein sires and their 1362 sons (19 to 102 sons per sire) were obtained from the Cooperative Dairy DNA Repository (CDDR), which is maintained by the USDA Bovine Functional Genomics Laboratory. In addition, 214 blood samples were obtained from the herd of the University of Wisconsin (UW herd). Predicted transmitting abilities (PTA) data for milk yield, milk protein and fat yields, milk protein and fat percentages, and SCS were obtained from the Animal Improvement Programs Laboratory. Summary statistics of PTA of both sons from the CDDR sire families and of cows from the UW herd for production and health traits is given in Table 3.

TABLE 3

Means, standard deviations (SD), and minimum, maximum, and average reliabilities (Rel) of predicted transmitting ability (PTA) of sons (from CDDR) and cows (UW herd) for production and health traits

| Trait | CDDR | | | | | UW herd | | | | |
|---|---|---|---|---|---|---|---|---|---|---|
| | Mean | SD | Min | Max | Rel | Mean | SD | Min | Max | Rel |
| Milk | 554 | 724 | −1743 | 2450 | 85.2 | 834 | 568 | −733 | 2375 | 55.6 |
| Fat | 18.40 | 22.41 | −59.00 | 81.00 | 85.2 | 28.34 | 20.34 | −27.00 | 87.00 | 55.6 |
| Protein | 21.84 | 20.21 | −55.00 | 85.00 | 85.1 | 27.11 | 15.05 | −19.00 | 67.00 | 55.6 |
| Fat % | −0.005 | 0.096 | −0.32 | 0.44 | 85.1 | −0.008 | 0.07 | −0.20 | 0.23 | 55.6 |
| Protein % | 0.023 | 0.044 | −0.14 | 0.18 | 85.1 | 0.01 | 0.03 | 0.09 | 0.11 | 55.6 |
| SCS | 3.14 | 0.16 | 2.68 | 3.71 | 70.5 | 3.12 | 0.13 | 2.74 | 3.53 | 40.6 |

Genotyping Genomic DNA was extracted from semen samples using proteinase K and phenol/chloroform after the procedures of Kappes et al. (2000) and from blood samples using GFX Genomic Blood DNA Purification Kit (Amersham Biosciences). The DNA concentration was measured using a spectrophotometer (Ultraspec 2100; Amersham Biosciences). A total of 1604 samples were genotyped in this study: 28 sires and their 1362 sons and 214 cows of the UW herd. In order to detect single nucleotide polymorphisms in OPN, different sets of primers were designed to amplify genomic sequences of the gene. Individuals were genotyped for a single nucleotide polymorphism (SNP) in intron 4 (GenBank accession number NW_255516) using the primers OPNF: GCAAATCAGAAGTGTGATAGAC (SEQ ID NO: 7) and OPNR: CCAAGCCAAACGTATGAGTT (SEQ ID NO: 8). Amplification of genomic DNA was performed in 25 µL of reaction volume, which included 50 ng of genomic DNA, 50 ng of each primer, 200 µM of each dNTP, 2.5 µL of 10×PCR buffer (Promega, Madison, Wis.), and 0.3 units of Taq DNA polymerase (Promega). The temperature cycles were as follows: 95° C. for 5 min; 32 cycles of 94° C. for 45 s, touchdown annealing from 63° C.-50° C. (−2° C./cycle) for 45 s, 72° C. for 45 s; and a final extension at 72° C. for 7 min. The PCR products were subjected to restriction fragment length polymorphism (RFLP) using the restriction enzyme BsrI that distinguishes alleles C and T of the SNP. The digestion products were electrophoresed on a 1.5% agarose gel; the T allele (uncut) was indicated by a band of 290 bp and the C allele was indicated by a band of 200 bp.

Statistical analysis Maternal allele frequencies of OPN were estimated following Thaller et al. (2003), where all sons from homozygous sires and all homozygous sons of heterozygous sires were used. The allele frequencies were estimated using the formula:

$$P_c = \frac{n_{CC} + n'_{TC}}{n_{CC} + n'_{TC} + n'_{TT} + n_{TT}}$$

where $n_{CC}$ and $n_{TT}$ are the number of homozygous CC and TT sons within heterozygous sires; $n'_{TC}$ and $n'_{TT}$ are the number of heterozygous TC and homozygous TT sons from homozygous TT sires. Weighted least squares analysis was employed to study the effects of OPN variants on production and functional traits in both the CDDR and UW herd populations. The model was $$y_{ij}=\mu+Sire_i+\beta x_{ij}+e_{ij},$$

where $y_{ij}$ is the PTA of the trait that was considered for son (CDDR)/daughter (UW herd) j of sire i, $Sire_i$ is the fixed effect of sire i, $\beta$ is the regression coefficient of PTA on the number of C alleles (0, 1, or 2) for jth son/daughter of sire i, and $e_{ij}$ is the residual. Reliability of the son's PTA was incorporated as weights in the model to obtain weighted least squares estimates for the allele substitution effects.

TABLE 4

Distribution of genotypes of sons for CDDR population.

| Sire genotype | Son genotypes | | |
| --- | --- | --- | --- |
| | CC | CT | TT |
| CC | 136 | 181 | 0 |
| CT | 181 | 392 | 196 |
| TT | 0 | 156 | 120 |

RESULTS AND DISCUSSION In this study, the frequencies of the OPN gene variants and their effects on milk production and health traits were examined in two independent Holstein populations. Table 4 shows the distribution of genotypes of sons and cows for the CDDR and UW herd populations, respectively. For the CDDR population, the number of sons per grandsire family ranged from 19 to 102 with an average of 49 sons per family. Seven sires were homozygous CC; seven sires were homozygous TT; and 14 sires were heterozygous. The estimated C allele frequency was 0.516 (±0.019). For the UW herd population, the frequencies of C and T alleles were 0.49 and 0.51, respectively. Thus, the frequencies of OPN alleles seem to be evenly distributed in both populations.

Table 5 shows the estimates of the allele substitution effects and their standard errors for production and health traits in the CDDR and UW herd populations. For the CDDR population, the C allele was associated with an increase in milk protein percentage (P=0.0255) and milk fat percentage (P=0.0480). The correlation between the two traits was 0.57 in the CDDR population (Khatib et al. 2005). OPN variants did not show significant effects on milk, fat, or protein yields or SCS. Although not statistically significant, allele C showed a negative effect on milk yield. This effect was not unexpected because of the negative correlation (−0.40) between this trait and milk protein percentage.

TABLE 5

Estimates of allele substitution effects and standard errors (SE) for production and health traits in the CDDR and UW herds

| Trait | CDDR population | | UW herd | |
| --- | --- | --- | --- | --- |
| | α/2 (SE) | P | α/2 (SE) | P |
| Milk yield | −28 (24) | 0.2491 | −61 (64) | 0.3474 |
| Milk fat yield | 0.86 (0.88) | 0.3229 | −0.78 (2.50) | 0.7554 |
| Milk fat % | 0.008 (0.004) | 0.048 | 0.005 (0.009) | 0.5623 |
| Milk protein yield | 0.12 (0.60) | 0.8481 | −0.38 (1.70) | 0.8264 |
| Milk protein % | 0.004 (0.002) | 0.0255 | 0.006 (0.005) | 0.2568 |
| SCS | −0.002 (0.006) | 0.7165 | −0.020 (0.017) | 0.2348 |

For the UW herd population, the estimates of the effects of allele C were in the same direction (negative for milk yield and positive for milk protein percentage) as for the CDDR population, although these estimates did not reach statistical significance level. This could be due to the small number of animals (214) that were available for genotyping and phenotyping and low reliabilities of PTA for the cows (Table 3). However, the results of the UW herd did not contradict the findings in the CDDR population. It is worth noting that the C allele did not show any significant unfavorable effects on the other examined traits.

The results above are consistent with other studies that have shown a significant association of microsatellite markers in the region of OPN with milk protein percentage and other correlated traits (Zhang et al. 1998; Mosig et al. 2001; Ron et al. 2001; Nadesalingam et al. 2001; Rodriguez-Zas et al. 2002; Ashwell et al. 2004; Olsen et al. 2004). Recently, Olsen and colleagues (2005) positioned a QTL affecting milk production traits to an interval of 420 kb between the genes ABCG2 (ATP-binding cassette, sub-family G (WHITE), member 2) and LAP3 (leucine aminopeptidase 3) on bovine chromosome 6. This narrow region harbours only six genes including OPN. While reporting this study, Schnabel et al. (2005) reported that OPN was associated with milk protein percentage in the CDDR population. They searched for SNPs in about 5 kb of sequence upstream of bovine OPN and identified 6 SNPs in which one SNP (a deletion/insertion) showed significant association with milk protein percentage.

Although the causative mutation was not found in the above study nor in other studies (Schnabel et al. 2005), it is concluded that OPN affects milk protein percentage or it is in linkage disequilibrium with other gene(s) that do. Further investigation of the OPN gene including upstream and downstream control regions is needed to elucidate molecular mechanisms causing the QTL effects.

References for Example 3

Ashwell, M. S., D. W. Heyen, T. S. Sonstegard, C. P. Van Tassell, Y. Da, P. M. VanRaden, M. Ron, J. I. Weller, and H. A. Lewin. 2004. Detection of quantitative trait loci affecting milk production, health, and reproductive traits in Holstein cattle. J. Dairy Sci. 87:468-475.

Bayless K. J., G. E. Davis, and G. A. Meininger. 1997. Isolation and biological properties of osteopontin from bovine milk. Protein Expr Purif. 9:309-314.

Denhardt, D. T., M. Noda, A. W. O'Regan, D. Pavlin, and J. S. Berman. 2001. Osteopontin as a means to cope with environmental insults: regulation of inflammation, tissue remodeling, and cell survival. J Clin Invest. 107:1055-1061.

Johnson G. A., R. C. Burghardt, F. W. Bazer, and T. E. Spencer. 2003. Osteopontin: roles in implantation and placentation. Biol Reprod. 69:1458-1471.

Kerr J. M., L. W. Fisher, J. D. Termine, and M. F. Young. 1991. The cDNA cloning and RNA distribution of bovine osteopontin. Gene 108:237-243.

Khatib H., E. Heifetz, and J. C. Dekkers. 2005. Association of the protease inhibitor gene with production traits in Holstein dairy cattle. J. Dairy Sci. 88:1208-1213.

Mosig M. O., E. Lipkin, G. Khutoreskaya, E. Tchourzyna, M. Soller, and A. Friedmann. 2001. A whole genome scan for quantitative trait loci affecting milk protein percentage in Israeli-Holstein cattle, by means of selective milk DNA pooling in a daughter design, using an adjusted false discovery rate criterion. Genetics 157:1683-1698.

Nadesalingam, J., Y. Plante, J. P. Gibson. 2001. Detection of QTL for milk production on Chromosomes 1 and 6 of Holstein cattle. Mammalian Genome 12:27-31.

Nagatomo, T., S. Ohga, H. Takada, A. Nomura, S. Hikino, M. Imura, K. Ohshima, and T. Hara. 2004. Microarray analysis of human milk cells: persistent high expression of osteopontin during the lactation period. Clin Exp Immunol. 138:47-53.

Olsen, H. G., S. Lien, M. Svendsen, H. Nilsen, A. Roseth, M. Aasland Opsal, and T. H. E. Meuwissen. 2004. Fine Mapping of Milk Production QTL on BTA6 by Combined Linkage and Linkage Disequilibrium Analysis. J. Dairy Sci. 87:690-698.

Olsen, H. G., S. Lien, M. Gautier, H. Nilsen, A. Roseth, P. R. Berg, K. K Sundsaasen, M. Svendsen, and T. H. Meuwissen. 2005. Mapping of a milk production quantitative trait locus to a 420-kb region on bovine chromosome 6. Genetics 169:275-283.

Rodriguez-Zas, S. L., B. R. Southey, D. W. Heyen, and H. A. Lewin. 2002. Detection of Quantitative Trait Loci Influencing Dairy Traits Using a Model for Longitudinal Data. J. Dairy Sci. 85:2681-2691.

Ron, M., D. Kliger, E. Feldmesser, E. Seroussi, E. Ezra, and J. I. Weller. 2001. Multiple quantitative trait locus analysis of bovine chromosome 6 in the Israeli Holstein population by a daughter design. Genetics 159:727-735.

Schnabel, R. D., J. J. Kim, M. S. Ashwell, T. S. Sonstegard, C. P. Van Tassell, E. E. Connor, and J. F. Taylor. 2005. Finemapping milk production quantitative trait loci on BTA6: Analysis of the bovine osteopontin gene. Proc Natl Acad Sci USA. 102:6896-6901.

Senger D. R., C. A. Perruzzi, A. Papadopoulos, and D. G. Tenen. 1989. Purification of a human milk protein closely similar to tumor-secreted phosphoproteins and osteopontin. Biochim Biophys Acta. 996:43-48.

Thaller, G., W. Kramer, A. Winter, B. Kaupe, G. Erhardt, and R. Fries. 2003. Effects of DGAT1 variants on milk production traits in German cattle breeds. J. Anim Sci. 81:1911-1918.

Zhang, Q., D. Biochard, I. Hoeschele, C. Ernst, A. Eggen, B. Murkve, M. Pfister-Genskow, L. A. Witte, F. E. Grignola, P. Uimari, G. Thaller, and M. D. Bishop. 1998. Mapping QTL for milk production and health of dairy cattle in a large outbred pedigree. Genetics 149:1959-1973.

Example 4

Milk Composition is Affected by a Quantitative Trait Nucleotide in the 3 Untranslated Region of the OLR1 Gene The oxidized form of the low density lipoprotein (oxLDL) is involved in endothelial cell injury, dysfunction, and activation, which is implicated in the development of atherosclerosis (1). It has been shown that oxLDL, and its lipid constituents, have numerous damaging effects on secretory activities of the endothelium, including the induction of apoptosis (2). The major protein, oxidized LDL receptor (OLR1), that binds, internalizes, and degrades oxLDL was initially identified in bovine aortic endothelial cells by Sawamura et al. (3). In addition to binding oxLDL, OLR1 removes aged/apoptotic cells from blood circulation (4). The bovine OLR1 cDNA encodes 270 amino acids with a 72% sequence identity to the human protein (3). Aoyama et al. (5) determined the structure of the human OLR1 gene to include six exons in which the first three exons corresponded to the N-terminal cytoplasmic, transmembrane, and connecting neck domains, and the last three exons encoded the lectin domain. The genomic sequence of the bovine OLR1 gene, recently released by the Baylor College of Medicine, contains five exons (GenBank accession no. NW_215807).

The exact location of the bovine OLR1 is not known, but based on combined data from different cattle genetic maps available in public databases, the present inventor mapped the gene at the interval of 106-108 cM of chromosome 5. Several quantitative trait loci (QTL) affecting milk production traits have been reported on bovine chromosome 5 in the vicinity of OLR1 gene (6). Heyen et al. (7) reported a putative QTL affecting fat percentage at a position 100 cM from the centromere in a large granddaughter and daughter design population composed of 1068 sons and 3264 daughters, respectively. Olsen et al. (8) reported that a QTL affecting fat yield at position 115 cM from the centromere. Also, Ashwell et al. (9) reported that a QTL located at 87 cM was associated with fat percentage in a North American Holstein population. QTL for other milk production traits in the OLR1 region were also reported. De Koning et al. (10) reported that a QTL at position 107 cM was associated with milk yield in the Finnish Ayrshire population. Using the same population, Viitala et al. (11) reported another QTL at position 98 cM that was associated with milk yield. QTL for milk yield was also reported at position 109 cM by Bennewitz et al. (12). For protein yield, Rodriguez-Zas et al. (13) reported that a QTL affecting this trait was located at position 91 cM.

Based on the abovementioned studies on the role of human OLR1 in lipid metabolism including degradation of oxLD and on previous QTL studies, the present inventor chose OLR1 as a candidate gene for association tests with milk production traits in dairy cattle. Several lines of evidence are presented here for a quantitative trait nucleotide (QTN) in the 3' untranslated region (UTR) that significantly increases fat yield and fat percentage in milk.

This gene appears to be the first marker gene identified in dairy cattle that affects fat content without negatively affecting other useful traits.

Materials and Methods

Population and phenotypic data. Semen samples from 29 Holstein sires and their 1433 sons were obtained from the Cooperative Dairy DNA Repository (CDDR), which is maintained by the USDA Bovine Functional Genomics Laboratory. Predicted transmitting abilities (PTA) data for milk yield, milk protein and fat yields, milk protein and fat percentages, productive life, and somatic cell score (SCS) were obtained from the USDA Animal Improvement Programs Laboratory. DNA samples from 19 Brown Swiss, 18 Bison bison, 15 Guernsey, 13 Jersey, 12 Bos indicus, and three Gaur individuals were included in this study for allele frequency comparisons.

Detection of single nucleotide polymorphisms (SNPs). SNPs were detected in the coding regions of the OLR1 gene by direct sequencing of RT-PCR products obtained from a pool of cDNAs from 50 animals. Total RNA was extracted from various bovine tissues, pooled, and used for RT-PCR amplification as previously described (1). The primers OLR5 (exon 1) 5'-ATGACTGTTGATGACCCCAAG-3' (SEQ ID NO: 9) and OLR6 (exon 5) 5'-CACTGTGCTCTCAATAGATTCGCCTT-3' (SEQ ID NO: 10) were designed to amplify the total cDNA sequence (812 bp) of the gene. SNPs in the 3'UTR were detected by direct sequencing of pooled DNA samples. Pools were constructed from 220 bovine DNA samples and amplified with unlabeled primers. Primers 3 (exon 5) 5'-AAGGCGAATCTATTGAGAGC-3' (SEQ ID NO: 11) and 4 (3' UTR) 5'-ACTTCTCTGAAGTCCTGCA-3' (SEQ ID NO: 12) were used to amplify genomic DNA sequence of 270 bp in the 3'UTR. PCR and RT-PCR products were sequenced and SNPs were identified by visually inspecting sequence traces.

DNA genotyping and haplotype construction. Genomic DNA was extracted from semen samples by standard method using proteinase K and phenol/chloroform. A total of 29 sires and their 1433 sons were genotyped in this study. For polymorphism at position 1070 (A/C) of OLR1 gene (accession no. D89049) all sons were genotyped using the restriction enzyme PstI. The digestion products were run out on a 3.0% agarose gel. The A allele (uncut) was indicated by a band at 270 bp and the C allele (cut) resulted in a band at 250 bp. For polymorphism at positions 603, five sires were heterozygous (C/T), a missence mutation in which Thrionine is replaced by Methionine. For polymorphism at position 604, a synonymous substitution, eight sires were heterozygous (A/G). All sons of the five sires that were heterozygous for the missense mutation were genotyped by direct sequencing for both 603 and 604 SNPs. Intragenic haplotypes were inferred as previously described (1).

Statistical analysis. Maternal allele frequencies of OLR1 were estimated following Thaller et al. (2003), where all sons from homozygous sires and all homozygous sons of heterozygous sires were used. The allele frequencies were estimated using the formula:

$$P_c = \frac{n_{CC} + n'_{AC}}{n_{CC} + n'_{AC} + n'_{AA} + n_{AA}}$$

where $n_{CC}$ and $n_{AA}$ are the number of homozygous CC and AA sons within heterozygous sires; $n'_{AC}$ and $n'_{AA}$ are the number of heterozygous AC and homozygous AA sons from homozygous AA sires.

For single SNP analysis, weighted least squares analysis was employed to study the effects of gene variants on production and functional traits. The model was $$y_{ij} = \mu + sire_i + bx_{ij} + e_{ij}$$

where $y_{ij}$ is the PTA of the trait that was considered for son j of sire i, sires is the fixed effect of sire i, b is the regression coefficient representing half of the gene substitution effect (Falconer and Mackey, 1996), $x_{ij}$ is the number of alleles (0, 1, or 2), and $e_{ij}$ is the residual. Reliability of the son's PTA was incorporated into the model to obtain weighted least squares estimates for the allele effects.

To test whether gene haplotypes have significant associations with the trait, an Allele Substitution Model was fitted to the PTA data (Batra et al., 1989; Weigel et al., 1990; Sharif et al., 1999). In this model, the most frequent haplotype was set to have zero effect. The allele substitution model has the structure:

$$Y_{ij} = \mu + sire_i + \sum_{k=1}^{M-1} \beta_k A_{ijk} + e_{ij}$$

where, $y_{ij}$ is the daughter yield deviation of the trait for son j of sire i, $\mu$ is the mean; $sire_i$ is the effect of sire i. $A_{ijk} = 0, 1, 2$, is the number of copies of haplotype k present in the $ij^{th}$ individual, where $A_0$ represents the most frequent of M marker haplotypes, and the remaining haplotypes are denoted $A_1, \ldots A_k, \ldots, A_{(M-1)}$; $\beta_k$ are partial regression coefficients corresponding to effect of haplotype k as a deviation from the effect of the most frequent haplotype ($A_0$), which is set to zero to make the model have full rank; $e_{ij}$ is the random error associated with the $ij^{th}$ individual. This model was fitted using weighted least squares, with weights based on reliability (Israel and Weller, 1998). Significance of associations was determined for each trait separately by an F-test on the sum of squares explained by the combined effect of haplotypes. Then, for traits with significant associations, estimates of the effect of individual haplotypes, as a deviation from the effect of the most frequent haplotype, were evaluated for significance.

Real-time PCR. Expression levels of OLR1 were evaluated by real-time PCR using a GeneAmp® 5700 Sequence Detection System (PE Biosystems) and PCR products were detected with SYBR Green I (Molecular Probes). A total of 33 RNA samples obtained from heart tissues were used in the real-time quantitative RT-PCR reactions. Each PCR reaction mix (25 μl) contained 1:20,000 dilution of SYRB Green I, 2.5 μl of 10×PCR Buffer (Promega), 1.5 mM $MgCl_2$, 200 μM dNTP, 250 nM forward primer, 250 nM reverse primer, 2 μl RT-PCR products, and 1.25 U Taq polymerase (Promega) (21). Thermal cycling conditions were 95° C. for 30 sec, followed by 40 cycles at 95° C. for 30 sec, 57° C. for 30 sec, and 72° C. for 30 sec, and finally 72° C. for 10 min. Melting curve analysis and agarose gel electrophoresis were performed after real-time PCR reaction to monitor PCR product purity.

The threshold cycle ($C_T$) numbers were determined for the amplified cDNA of the bovine OLR1 mRNA and for the housekeeping gene, acidic ribosomal phosphoprotein (PO), in each sample from different tissues during real-time PCR (22). The relative quantification of OLR1 gene expression in different tissues was evaluated using a standard curve method. Standard curves for PCR amplification of cDNAs of OLR1 and PO genes were constructed using purified PCR products of the mRNAs of the two genes and five serial dilutions of the products were used ranging from 1024 to 1 attograms (23). Standard curves were generated by plotting the $C_T$ values (y-axis) against the logarithm of input purified PCR products α-axis). For each sample, the amount of OLR1 and PO was determined from the standard curve. Then, the amount of OLR1 was divided by the amount of PO to obtain a normalized OLR1 value expressed as the ratio of OLR1/PO.

Results

Estimation of allele and haplotype frequencies in cattle breeds. Direct sequencing of pooled RT-PCR products for the total coding sequence of OLR1 revealed two SNPs in exon 4 at positions 603 (C/T) and 604 (A/G). SNP 603 is a missense mutation in which thrionine is replaced by methionine and SNP 604 is a synonymous substitution. Direct sequencing of genomic DNA at 3'UTR of OLR1 revealed one SNP (A/C) at position 1070. Four intragenic haplotypes (1=CAA; 2=CAC; 3=CGC; 4=TGC) comprising positions 603, 604, and 1070 were inferred in a sample of 633 individuals from the CDDR resource population. The frequencies of haplotype 1, 2, 3, and 4 were 0.725, 0.170, 0.052, and 0.043, respectively.

The allele frequencies of OLR1 variants at SNP 1070 were estimated in 1433 Holstein bulls, 19 Brown Swiss, 18 Bison bison, 15 Guernsey, 13 Jersey, 12 Bos indicus, and in three Gaur individuals. The C allele frequency was 0.54 (standard error=0.018) in Holstein bulls, 0.87 in Guernsey, and 0.83 in Bos indicus. The C allele was predominant in Bison bison, Brown Swiss, Jersey, and Gaur individuals. For the CDDR Holstein population, the number of sons per grandsire family ranged from 18 to 99 with an average of 49 sons per family. Seven sires were homozygous CC, eight sires were homozygous AA, and 14 sires were heterozygous.

Effects of the OLR1 haplotypes on production traits in the CDDR Holstein population. An allele substitution model, in which haplotype 1 was set to have zero effect, was used to estimate the effects of OLR1 haplotypes on milk production and health traits in Holstein population. Table 9 shows the analysis of the effects of OLR1 region which combines information of all haplotypes together. The OLR1 region as a whole showed a strong effect on fat percentage (P=0.00001), fat yield (P=0.00058), and productive life (P=0.02442). In contrast, OLR1 region did not show significant effects on milk yield, protein yield and percentage, and SCS. Table 10 shows the estimates of the substitution effects of the OLR1 haplotypes for milk production and health traits as a deviation from the effect of haplotype 1. Haplotype 2 was associated with a significant increase in fat yield (P=0.0166) and in fat percentage (P=0.0038). Haplotype 3 showed a suggestive association with productive life (0.1084) and haplotype 4 did not show significant effects on any of the examined traits.

TABLE 9

Significance of effects of OLR1 gene region on production and health traits

| Trait | F-test | P |
|---|---|---|
| Milk yield | 0.61 | 0.61187 |
| Fat yield | 5.89 | 0.00058 |
| Fat percentage | 9.28 | 0.00001 |
| Protein yield | 1.06 | 0.36462 |
| Protein percentage | 0.35 | 0.78882 |
| Productive life | 3.15 | 0.02442 |
| SCS | 1.51 | 0.21099 |

TABLE 10

Estimates of substitution effects of OLR1 haplotypes for milk production and health traits as a deviation from effect of the most frequent haplotype (1).

| Trait | Haplotype 1 | Haplotype 2 | Haplotype 3 | Haplotype 4 |
|---|---|---|---|---|
| Milk yield | 0.00 | −6.7 ± 43.9 | −3.82 ± 75.6 | −50.5 ± 65.7 |
| Fat yield | 0.00 | 3.82 ± 1.59** | −0.94 ± −0.34 | 0.46 ± 0.19 |
| Fat % | 0.00 | 0.021 ± 0.007*** | −0.004 ± 0.012 | 0.0112 ± 0.010 |
| Protein yield | 0.00 | 0.19 ± 1.09 | −0.16 ± 1.88 | −1.63 ± 1.64 |
| Protein % | 0.00 | 0.0018 ± 0.0032 | 0.0004 ± 0.0055 | −0.0004 ± 0.0048 |
| Productive life | 0.00 | −0.002 ± 0.082 | 0.229 ± 0.143* | 0.126 ± 0.123 |
| SCS | 0.00 | −0.006 ± 0.012 | −0.023 ± 0.021 | −0.001 ± 0.018 |

*P = 0.1084;
**P = 0.0166;
***P = 0.0038

Effects of single SNPs on production traits. To study the effects of OLR1 variants on production and functional traits, a single SNP analysis was performed for each of the three polymorphic sites at positions 603, 604, and 1070. Analysis of SNPs 603 and 604 did not show any significant effects on any of the examined traits (data not shown). In contrast, analysis of SNP 1070 revealed significant effects on both fat yield and fat percentage.

Table 11 shows estimates of the allele substitution effects for production and functional traits in 1433 individuals from the CDDR population. Allele C was associated with a significant increase in fat yield (P=0.0013) and fat percentage (P=0.0006). It is worth noting that allele C did not show any significant unfavorable effects on the other examined traits.

TABLE 11

Estimates of allele substitution effects (of allele C at SNP 1070) and standard errors for production and functional traits in CDDR population.

| Trait | α/2 (SE) | P |
|---|---|---|
| Milk yield | −1.54 (25.08) | 0.9510 |
| Fat yield | 2.98 (0.92) | 0.0013 |
| Fat percentage | 0.014 (0.004) | 0.0006 |
| Protein yield | 0.21 (0.63) | 0.7369 |
| Protein percentage | 0.001 (0.001) | 0.5296 |
| Productive life | 0.06 (0.05) | 0.2100 |
| SCS | 0.005 (0.006) | 0.4825 |

The results on the effects of haplotype 2, which has C at position 1070, and the results of the single SNP analysis of allele C of SNP 1070 motivated us to estimate the substitution effects of haplotypes 3 and 4 for fat yield and fat percentage as a deviation from the effect of haplotype 2. These two haplotypes has also C at position 1070, hence significant differences between haplotypes 3 and 4 and haplotype 2 would point to the presence of additional SNP/s at haplotype 2 affecting fat yield and fat percentage. Table 12 shows the estimates of the substitution effects of the OLR1 haplotypes for fat yield and fat percentage as a deviation from the effect of haplotype 2. For fat yield, haplotypes 3 and 4 did not show significant associations, while for fat percentage haplotype 3 showed a suggestive association (P=0.0854) and haplotype 4 did not show significant association.

TABLE 12

Estimates of the substitution effects of the OLR1 haplotypes for fat yield and fat percentage as a deviation from the effect of haplotype 2.

| Haplotype | Fat yield | P | Fat percentage | P |
|---|---|---|---|---|
| 1 | −3.82 ± (1.59) | 0.0166 | −0.021 ± 0.007 | 0.0038 |
| 2 | 0.00 | | 0.00 | |
| 3 | −4.76 ± (3.17) | 0.1340 | −0.025 ± 0.014 | 0.0854 |
| 4 | −3.69 ± (2.74) | 0.2222 | −0.010 ± 0.012 | 0.4328 |

Expression analysis of OLR1 transcripts in heart tissues. To test the expression level of OLR1 in individuals with C allele compared to individuals with T allele at SNP 1070, fetuses and dams were first genotyped using RFLP-PCR and direct genomic sequencing. Then, expression levels of OLR1 in 33 hearts from these individuals were evaluated using real-time quantitative RT-PCR (FIG. 5). The level of expression of OLR1 transcripts in relation to PO transcripts was considerably lower in individuals bearing genotype AA (OLR1/PO ratio=35.4) compared to CC individuals (OLR1/PO ratio=170.5). The OLR1/PO ratio in heterozygous individuals was 77.4. Thus, C at position 1070 in the 3'UTR may be the functional nucleotide that increases fat yield and percentage in cow milk.

In summary, nucleotide C at position 1070 in the 3' UTR of OLR1 gene has been shown to have a positive effect on milk fat yield and milk fat percentage in dairy cattle. The positional comparative candidate gene analysis and previous QTL linkage mapping results were used to select the OLR1 gene as a candidate gene affecting milk production traits. To search for polymorphic sites in the gene, pools of cDNAs extracted from a wide range of cattle tissues and pools of genomic DNA extracted from semen samples were sequenced. Using the pooled sequencing approach, two SNPs at positions 603 and 604 in exon 4 and one SNP at position 1070 in the 3' UTR were identified. SNP 603 (C/T) is a missense mutation in which thrionine is replaced by methionine and SNP 604 (A/G) is a synonymous mutation.

The first three exons of the human OLR1 correspond to cytoplasmic domain, transmembrane domain, and the neck domain whereas exons 4-6 encode the lectin-like domain (5). Chen et al. (25) conducted series of targeted mutations in the lectin-like domain to identify structures required for oxLDL binding. They found that the lectin-like domain is essential for binding and endocytosis of oxLDL. To test whether the thrionine/methionine SNP 603-found in exon 4 of the bovine gene that encodes the lectin-like domain—is associated with milk yield and composition traits, the 29 Holstein sires of the CDDR population were genotyped. Genotyping revealed five sires heterozygous for SNP 603, eight sires heterozygous for SNP 604, and 14 sires heterozygous for SNP 1070. All sons of the five sires heterozygous for SNP 603 were genotyped by direct sequencing for both 603 and 604 SNPs. Four intragenic haplotypes including SNPs 603, 604, and 1070 were identified in the CDDR population and tested for association with milk production traits. Only haplotype 2 (C-A-C) was associated with a significant increase in fat yield and fat percentage. Thus, it is concluded that the amino acid substitution at position 603 (included in haplotype 4) was not responsible for the effects of OLR1 on fat yield and fat percentage.

To search for the causative mutation in haplotype 2, two analyses were performed; a single SNP analysis for each of the three individual SNPs and a haplotype analysis. The results of the single SNP analysis showed that allele C of SNP 1070 had significant effects on fat yield and percentage whereas SNPs 603 and 604 had no significant effects. Given that haplotypes 2, 3 and 4 include C nucleotide at position 1070 and that only haplotype 2 showed significant associations, the allele substitution model was used to estimate the effects of haplotypes 3 and 4 as a deviation from the effect of haplotype 2. The results show that the effects of haplotype 2 were not significantly different from the effects of haplotypes 3 and 4. Thus, both single SNP analysis and haplotype analysis strongly indicate that SNP 1070 in the 3'UTR might be the causative mutation affecting milk fat yield and percentage. To search for other SNPs in the 3'UTR, a total of 790 bp of genomic DNA from all 29 sires were sequenced, but no SNPs were identified.

To provide support for the hypothesis that SNP 1070 is the QTN responsible for OLR1 effects, the expression levels of OLR1 in individuals bearing different genotypes were assessed. It was found that OLR1 expression was reduced in AA individuals compared to CC and AC individuals, suggesting that A at position 1070 may be the nucleotide decreasing OLR1 expression.

It is of note that two independent studies on the human gene reported, surprisingly, that a SNP (C/T) in the 3' UTR, at position 1073, was associated with Alzheimer's disease (AD). Luedecking-Zimmer et al. (25) reported that among three SNPs identified in OLR1, the 3'UTR polymorphism showed the most significant association with AD. Moreover, they showed that the C allele at this position had a higher affinity for binding regulatory proteins compared to the T allele. Also, Lambert et al. (26) presented additional evidence that the 3' UTR polymorphism was associated with AD. Using electrophoretic mobility shift assays, they found that the C allele was associated with higher binding affinity of nuclear proteins. In addition, they showed that the expression level of OLR1 was lower in individuals bearing CC genotypes compared to CT and TT individuals.

The exact mechanism by which the bovine OLR1 variants can affect milk fat yield and milk fat percentage is not clear. However, given that OLR1 is a receptor for oxLDL and that it is expressed abundantly in heart, it might affect directly the metabolism of oxLDL which in turn affects fat metabolism. In fact, the hypothesis that human OLR1 variants might be involved in heart diseases was tested in two independent studies. Mango et al. (27) showed that the 3' UTR SNP was associated with higher risk of developing acute myocardial infarction. Also, Chen et al. (28) reported association of the 3'UTR SNP with coronary artery disease. Moreover, using electrophoretic mobility shift assay, they found that the 3' UTR SNP affects the binding of a putative transcription factor in an allele-specific manner. Thus, while not willing to be bound by any theory, it is believed that the 3' UTR SNP of the present invention that affects milk fat yield and milk fat percentage, might affect mRNA stability or translation of the OLR1 as it was predicted for the human gene (28). There is growing evidence that 3' UTR sequences are involved in the regulation of gene expression and they can control stability of mRNA, polyadenylation, rates of translation, nuclear transport, and gene silencing (29). Recently, Oliver et al. (30) reported that a 3'UTR polymorphism in the Gpc3 gene, a candidate gene chosen based on QTL studies, affects high growth in mice.

Estimation of allele frequencies of OLR1 in different cattle breeds was an additional support for the hypothesis that SNP 1070 is the actual QTN affecting fat yield and percentage. It has long been known that Bison bison, Brown Swiss, Jersey, and Guernsey breeds have higher fat percentage than the Holstein breed. Surprisingly, it was found that the frequency of the C allele of SNP 1070—that is associated with an increase in fat yield and fat percentage in the Holstein population—was 54% in the Holsteins, whereas its frequency in Bison bison, Brown Swiss, and Jersey populations was 100% and its frequency in Guernsey was 87%.

Thus, several lines of evidence show that SNP 1070 is the QTN.

References to Example 4

1. Mehta, J. L. & Li, D. Y. (1998) Identification and autoregulation of receptor for OX-LDL in cultured human coronary artery endothelial cells. Biochem. Biophys. Res. Commun. 248, 511-514.
2. Imanishi, T., Hano, T., Sawamura, T., Takarada, S. & Nishio I. (2002) Oxidized low density lipoprotein potentiation of Fas-induced apoptosis through lectin-like oxidized-low density lipoprotein receptor-1 in human umbilical vascular endothelial cells. Circ. J. 66, 1060-1064.

3. Sawamura, T., Kume, N., Aoyama, T., Moriwaki, H., Hoshikawa, H., Aiba, Y., Tanaka, T., Miwa, S., Katsura, Y., Kita, T. et al. (1997) An endothelial receptor for oxidized low-density lipoprotein. *Nature* 386, 73-77.

4. Oka, K., Sawamura, T., Kikuta, K., Itokawa, S., Kume, N., Kita, T. & Masaki, T. (1998) Lectin-like oxidized low-density lipoprotein receptor 1 mediates phagocytosis of aged/apoptotic cells in endothelial cells. *Proc. Natl. Acad. Sci. USA* 95, 9535-9540.

5. Aoyama, T., Sawamura, T., Furutani, Y., Matsuoka, R., Yoshida, M. C., Fujiwara, H. & Masaki, T. (1999) Structure and chromosomal assignment of the human lectin-like oxidized low-density-lipoprotein receptor-1 (LOX-1) gene. *Biochem. J.* 339, 177-84.

6. Khatkar, M. S., Thomson, P. C., Tammen, I. & Raadsma, H. W. (2004) Quantitative trait loci mapping in dairy cattle: review and meta-analysis. *Genet. Sel. Evol.* 36, 163-190.

7. Heyen, D. W., Weller, J. I., Ron, M., Band, M., Beever, J. E., Feldmesser, E., Da, Y., Wiggans, G. R., VanRaden, P. M. & Lewin, H. A. (1999) A genome scan for QTL influencing milk production and health traits in dairy cattle. *Physiol. Genomics* 1, 165-175.

8. Olsen, H. G., Gomez-Raya, L., Vage, D. I., Olsaker, I., Klungland, H., Svendsen, M., Adnoy, T., Sabry, A., Klemetsdal, G. Schulman, N. et al. (2002) A genome scan for quantitative trait loci affecting milk production in Norwegian dairy cattle. *J. Dairy Sci.* 85, 3124-3130.

9. Ashwell, M. S., Heyen, D. W., Sonstegard, T. S., Van Tassell, C. P., Da, Y., VanRaden, P. M., Ron, M., Weller, J. I. & Lewin, H. A. (2004) Detection of quantitative trait loci affecting milk production, health, and reproductive traits in Holstein cattle. *J. Dairy Sci.* 87, 468-475.

10. de Koning, D. J., Schulmant, N. F., Elo, K., Moisio, S., Kinos. R., Vilkki, J., & Maki-Tanila, A. (2001) Mapping of multiple quantitative trait loci by simple regression in half-sib designs. *J. Anim Sci.* 79, 616-622.

11. Viitala, S. M., Schulman, N. F., de Koning, D. J., Elo, K., Kinos, R., Virta, A., Virta, J., Maki-Tanila, A. & Vilkki, J. H. (2003) Quantitative trait loci affecting milk production traits in Finnish Ayrshire dairy cattle. *J. Dairy Sci.* 86, 1828-1836.

12. Bennewitz, J., Reinsch, N., Grohs, C., Leveziel. H., Malafosse, A., Thomsen, H., Xu, N., Looft, C., Kuhn, C., Brockmann, G. A. et al. (2003) Combined analysis of data from two granddaughter designs: A simple strategy for QTL confirmation and increasing experimental power in dairy cattle. *Genet. Sel. Evol.* 35, 319-338.

13. Rodriguez-Zas, S. L., Southey, B. R., Heyen, D. W. & Lewin, H. A. (2002) Interval and composite interval mapping of somatic cell score, yield, and components of milk in dairy cattle. *J. Dairy Sci.* 85, 3081-3891.

14. Khatib, H., Heifetz, E. & Dekkers, J. C. (2005) Association of the protease inhibitor gene with production traits in Holstein dairy cattle. *J. Dairy Sci.* 88, 1208-1213.

15. Thaller, G., Kramer, W., Winter, A., Kaupe, B., Erhardt, G. & Fries, R. (2003) Effects of DGAT1 variants on milk production traits in German cattle breeds. *J. Anim Sci.* 81, 1911-1918.

16. Falconer, D. S. & Mackay T. F. C. (1996) *Quantitative genetics.* (Addison Wesley Longman Ltd., Essex, England).

17. Batra, T. R., Lee, A. J. & Gavora, J. S. (1989). Class I alleles of the bovine major histocompatibility system and their association with economic traits. *J. Dairy Sci.* 72, 2115-2124.

18. Weigel, K. A., Kehrli, M. E. J. R., Stear, M. J. & Kelley, D. H. (1990) Association of class I bovine lymphocyte antigen complex alleles with health and production traits in dairy cattle. *J. Dairy Sci.* 73, 2538-2546.

19. Sharif S., Mallard B. A., Wilkie, B. N., Sargeant, J. M., Scott, H. H., Dekkers, J. C. & Leslie, K. E. (1999) Association of the bovine major histocompatibility complex DRB3 (BoLA-DRB3) with production traits in Canadian dairy cattle. *Animal Genetics* 30, 157-160.

20. Israel, C. & Weller, J. I. (1998) Estimation of candidate gene effects in dairy cattle populations. *J. Dairy Sci.* 81, 1653-1662.

21. Karsai, A., Muller, S., Platz, S. & Hauser, M. T. (2002) Evaluation of a homemade SYBR green I reaction mixture for real-time PCR quantification of gene expression. *Biotechniques* 32, 790-796.

22. Bieche, I., Nogues, C., Paradis, V., Olivi, M., Bedossa, P., Lidereau, R. & Vidaud, M. (2000) Quantitation of hTERT gene expression in sporadic breast tumors with a real-time reverse transcription-polymerase chain reaction assay. *Clin. Cancer Res.* 6, 452-459.

23. Robert, C., McGraw, S., Massicotte, L., Pravetoni, M., Gandolfi, F. & Sirard, M. A. (2002) Quantification of Housekeeping Transcript Levels During the Development of Bovine Preimplantation Embryos. *Biol. Reprod.* 67, 1465-1472.

24. Chen, M., Narumiya, S., Masaki, T. & Sawamura, T. (2001) Conserved C-terminal residues within the lectin-like domain of LOX-1 are essential for oxidized low-density-lipoprotein binding. *Biochem J.* 355, 289-296.

25. Luedecking-Zimmer, E., DeKosky, S. T., Chen, Q., Barmada, M. M. & Kamboh, M. I. (2002) Investigation of oxidized LDL-receptor 1 (OLR1) as the candidate gene for Alzheimer's disease on chromosome 12. *Hum. Genet.* 111, 443-451.

26. Lambert, J. C., Luedecking-Zimmer, E., Merrot, S., Hayes, A., Thaker, U., Desai, P., Houzet, A., Hermant, X., Cottel, D., Pritchard, A. et al. (2003) Association of 3'-UTR polymorphisms of the oxidised LDL receptor 1 (OLR1) gene with Alzheimer's disease. *J. Med. Genet.* 40, 424-430.

27. Mango, R., Clementi, F., Borgiani, P., Forleo, G. B., Federici, M., Contino, G., Giardina, E., Garza, L., Fahdi, I. E., Lauro, R. Et al. (2003) Association of single nucleotide polymorphisms in the oxidised LDL receptor 1 (OLR1) gene in patients with acute myocardial infarction. *J. Med. Genet.* 40, 933-936.

28. Chen, Q., Reis, S. E., Kammerer, C., Craig, W. Y., LaPierre, S. E., Zimmer, E. L., McNamara, D. M., Pauly, D. F., Sharaf, B., Holubkov, R. et al. (2003) Genetic variation in lectin-like oxidized low-density lipoprotein receptor 1 (LOX1) gene and the risk of coronary artery disease. *Circulation* 107, 3146-3151.

29. Conne, B., Stutz, A. & Vassalli, J. D. (2000) The 3' untranslated region of messenger RNA: A molecular 'hotspot' for pathology? *Nat. Med.* 6, 637-641.

30. Oliver, F., Christians, J. K., Liu, X., Rhind, S., Verma, V., Davison, C., Brown, S. D., Denny, P. & Keightley, P. D. (2005) Regulatory variation at glypican-3 underlies a major growth QTL in mice. *PLoS. Biol.* 3, e135.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations and equivalents falling within the scope of the appended claims and equivalents thereof. All references cited hereinabove and/or listed below are hereby expressly incorporated by reference.

What is claimed is:

1. An isolated nucleic acid molecule comprising position 1070 of SEQ ID NO: 4, and at least 20 contiguous nucleotides of SEQ ID NO: 4 adjacent to position 1070, wherein position 1070 is adenosine.

2. An isolated nucleic acid molecule according to claim 1, which comprises not more than 150 nucleotides.

3. An isolated nucleic acid molecule according to claim 1, which comprises not more than 100 nucleotides.

4. An isolated nucleic acid molecule according to claim 1, which comprises not more than 50 nucleotides.

5. A nucleic acid molecule according to claim 1, wherein position 1070 is within 4 nucleotides of the center of the nucleic acid molecule.

6. A nucleic acid molecule according to claim 5, wherein position 1070 is at the center of the nucleic acid molecule.

7. A nucleic acid molecule according to claim 1, wherein position 1070 is at the 3'-end of the nucleic acid molecule.

8. A kit comprising a nucleic acid molecule of claim 1, and a suitable container.

9. An isolated nucleic acid molecule consisting of not more than 25 nucleotides, wherein the nucleic acid molecule comprising position 1070 of SEQ ID NO: 4, and at least 20 contiguous nucleotides of SEQ ID NO: 4 adjacent to position 1070, wherein position 1070 is adenosine.

* * * * *